(12) United States Patent
Tulip

(10) Patent No.: US 9,755,399 B2
(45) Date of Patent: Sep. 5, 2017

(54) PACKAGED LASER THERMAL CONTROL SYSTEM

(71) Applicant: Boreal Laser Inc., Edmonton (CA)

(72) Inventor: John Tulip, Edmonton (CA)

(73) Assignee: Boreal Laser Inc., Edmonton (CA)

(*) Notice: Subject to any disclaimer, the term of this patent is extended or adjusted under 35 U.S.C. 154(b) by 0 days.

(21) Appl. No.: 15/145,446

(22) Filed: May 3, 2016

(65) Prior Publication Data

US 2016/0329681 A1 Nov. 10, 2016

Related U.S. Application Data

(60) Provisional application No. 62/157,009, filed on May 5, 2015.

(51) Int. Cl.
  *H01S 5/024* (2006.01)
  *H01S 5/068* (2006.01)
  *G01N 21/39* (2006.01)
  *H01S 5/022* (2006.01)

(52) U.S. Cl.
  CPC ......... *H01S 5/02415* (2013.01); *G01N 21/39* (2013.01); *H01S 5/06804* (2013.01); *G01N 2021/399* (2013.01); *H01S 5/02216* (2013.01); *H01S 5/02284* (2013.01); *H01S 5/02476* (2013.01)

(58) Field of Classification Search
  CPC ............. H01S 5/02415; H01S 5/06804; H01S 5/02216; H01S 5/02284; G01N 21/39; G01N 2021/399
  See application file for complete search history.

(56) References Cited

U.S. PATENT DOCUMENTS

| 6,055,815 A * | 5/2000 | Peterson | H01S 3/042 62/259.2 |
|---|---|---|---|
| 6,658,034 B2 | 12/2003 | Garnache et al. | |
| 8,288,727 B2 | 10/2012 | Cormier et al. | |

FOREIGN PATENT DOCUMENTS

WO 2015/159049 A1 10/2015

OTHER PUBLICATIONS

Webster, C.R. "Brewster-plate spoiler: a novel method for reducing the amplitude of interference fringes that limit tunable-laser absorption sensitivities," J. Opt. Soc. Am. B/vol. 2, No. 9, Sep. 1985, pp. 1464-1470.
Ikegami, T., et al. "Frequency Stabilization of semiconductor laser diodes," Artech House, 1995, 13 pgs.
(Continued)

*Primary Examiner* — Dung Nguyen
(74) *Attorney, Agent, or Firm* — Seed IP Law Group LLP

(57) ABSTRACT

A thermal stabilization system for a packaged diode laser. An outer thermoelectric cooler (TEC) stabilizes the temperature of the laser package and an inner TEC stabilizes the temperature of the laser diode element of the packaged laser. The inner and outer TECs may be controlled by electronics which is also stabilized in temperature, for example using resistive heating. The packaged laser may be mounted on a heat spreader mounted on the outer TEC and may be surrounded by an insulated covering on all sides other than the surface mounted on the heat spreader. There may also be a thermally conductive cap over the packaged laser, with the insulation arranged outside the cap if both are present.

22 Claims, 4 Drawing Sheets

(56) References Cited

OTHER PUBLICATIONS

Sandford, S. P., et al. "Laser Frequency Control Using an Optical Resonator Locked to an Electronic Oscillator," IEEE Journal of Quantum Electronics, vol. 33, No. 11, Nov. 1997, pp. 1991-1996.
Ackerman, D. A., et al. "Low-Cost Athermal Wavelength-Locker Integrated in a Temperature-Tuned Single-Frequency Laser Package," Journal of Lightwave Technology, vol. 22, No. 1, Jan. 2004, pp. 166-171.
Van Well, B., et al. "An open-path, hand-held laser system for the detection of methane gas," Journal of Optics A: Pure and Applied Optics, vol. 7 No. 6, 2005 pp. S420-S424.
Asmari, A. et al. "Wavelength stabilisation of a DFB laser diode using measurement of junction voltage," Proc. of SPIE, vol. 9135, 91351A, May 1, 2014, 2 pgs.
Asmari, A. "A novel laser diode wavelength stabilization technique for use in high resolution spectroscopy," Cranfield University, School of Engineering, PhD Thesis, Academic Year 2014-2015, 193 pgs.

* cited by examiner

PACKAGED LASER THERMAL CONTROL SYSTEM

CROSS-REFERENCE TO RELATED APPLICATIONS

This application claims the benefit under 35 U.S.C. §119(e) of U.S. Application No. 62/157,009, filed May 5, 2015.

BACKGROUND

Technical Field

This invention in general relates to gas monitors used, for example, in the process industry. In particular this invention relates to improvements in detection and measurement of gas concentrations and gas emissions based on tunable diode lasers.

Description of the Related Art

Accurate monitoring of gaseous species at low concentrations is required for a wide range of industrial, regulatory, and academic fields. The most common include atmospheric chemistry, pollution monitoring, industrial process monitoring and control, safety, breath analysis, and agricultural research. One of the most reliable principles for continuous monitoring of gases is the measurement of gas absorption since most gases have one or more absorption lines in the ultra violet, visible or the infrared part of the spectrum. This technique is known as absorption spectroscopy. With this method a beam of light such as a laser beam that is absorbed by the gas of interest, is directed through the gas or a mixture of gases. The degree of absorption of the light beam is then used as an indicator for the concentration of the gas to be detected. Many different spectroscopic techniques exist, but the use of single line spectroscopy utilizing single mode tunable diode lasers is probably the one giving best sensitivity and selectivity due to its high spectral resolution involving a low risk of interference from other gases.

There are two popular spectroscopic methods of laser gas detection. In one the frequency of the laser is rapidly scanned across the gas absorption line by modulation of the laser diode current. Gas absorption results in modulation of the amplitude of the transmitted light and this amplitude can be measured using a photodetector and simple electronics. The absorption of the laser beam on-line and off-line may be compared and the gas absorption and concentration computed. This is method is referred to by several names including scanned direct absorption and rapid scan absorption. This method has the advantage of simplicity but it can be difficult to establish a zero absorption baseline. The other popular method is called modulation spectroscopy; the most commonly used is referred to as wavelength modulation spectroscopy (WMS). In this method the laser frequency and amplitude is modulated using laser current as in the case of direct absorption. In addition, the laser current is also modulated at a second relatively high frequency. Gas absorption distorts the amplitude of the modulated laser light so that harmonics of the high modulation frequency appear after the beam has passed through a gas. These harmonics are measured by demodulating the gas signal. Sensitive tunable diode laser (TDL) absorption measurements have been performed for decades with wavelength modulation spectroscopy (WMS) for a wide variety of practical applications. With its better noise-rejection characteristics through laser wavelength modulation strategies, WMS has long been recognized as the method of choice for sensitive measurements of small values of absorption, and thus is favored for trace species detection.

Laser diode wavelength stability is vital in tunable diode laser spectroscopy (TDLS). Since both laser diode threshold current and laser emission wavelength are functions of temperature, laser diode temperature stability is very important in laser spectroscopy. For example, the commonly used 1651 nm atmospheric absorption line of methane has a linewidth (HWHM) of 50 picometers (pm). Laser spectroscopy requires the wavelength precision of the laser to be substantially less than this linewidth.

TDLS gas sensing systems, the laser diode temperature is controlled with a thermoelectric cooler (TEC). The laser die is typically mounted in close proximity to a Peltier element and a temperature-sensing thermistor. The TEC controlling circuit uses current from the thermistor in a feedback loop with the Peltier element to regulate temperature of the thermistor and the laser diode. It is possible and practicable to regulate the temperature of the Peltier element to less than 1 milli-kelvin. However, even with good thermal design internal temperature gradients exist between the laser die and the thermistor because of both ambient temperature changes and laser die heating. A change in ambient temperature consequently causes a change in the laser temperature and this laser temperature change results in a systematic error in the laser diode emission wavelength. Typically the laser emission wavelength changes by 5 pm for each centigrade change in ambient temperature. An ambient change of 30 C will result in a laser emission wavelength change of 150 pm which is the equivalent to approximately three line widths of the 1651 nm methane line. A change in ambient temperature by only one degree will typically result in 5 pm change in laser emission wavelength which is typically 10% of a gas absorption linewidth and unacceptable for TDLS spectroscopy.

Thermal changes in the TEC and laser current generating circuitry also cause TDLS systems to drift. This drift is relatively small but is important for applications requiring high precision and accuracy. Electronic components are sensitive to temperature and dissimilar metals in a circuit board create thermoelectric voltages that change with the temperature of the circuitry. Even in carefully designed circuitry ambient temperature changes result in changes in TEC control currents and laser currents that cause the laser emission frequency to drift when the ambient temperature changes.

Several methods have been proposed to stabilize the emission wavelength of diode lasers.

{T. Ikegami, S. Sudo, Y. Sakai, "Frequency Stabilization of semiconductor laser diodes" Artech House, (1995)}

The commonest method is to use a sample of the target gas contained in a reference cell.

{Van Well, B., Murray, S., Hodgkinson, J., Pride, R., Strzoda, R., Gibson, G. and Padgett, M., "An open-path, hand-held laser system for the detection of methane gas," J. Opt. A—Pure Appl. Opt. 7, S420-S424 (2005)}

Gas reference cells are commonly used as absolute wavelength standards.

{Gilbert, S. L., Swann, W. C. and Dennis, T., "Wavelength standards for optical communications," Proc. SPIE 4269, 184-191 (2001)}

When a gas reference cell is used to stabilize emission wavelength in a TDLS system, the system typically has an optical reference path that contains the gas reference cell. The system analyzer captures the spectrum of the sample gas and uses a feedback loop to stabilize the laser emission wavelength and prevent wavelength drift. This is known in the art as line centering. The system adjusts emission wavelength by changing either the laser temperature or the laser injection current. This method has the disadvantages of adding substantial opto-mechanical complexity and with even the most careful design can introduce optical interference effects and degrade system sensitivity. Adjustment of the laser current or temperature by the system during line centering also typically causes changes of laser light amplitude and instrument calibration.

Other laser wavelength stabilization methods use athermalised etalons and electrically stabilized optical resonators as wavelength standards. These methods share the same disadvantages as the gas cell wavelength standard.

{Ackerman, D. A., Paget, K. M., Schneemeyer, L. F., Ketelsen, L. J.-P., Warning, F. W., Sjolund, O., Graebner, J. E., Kanan, A., Raju, V. R., Eng, L. E., Schaeffer, E. D. and Van Emmerik, P., "Low-cost athermal wavelength locker integrated temperature-tuned single-frequency laser package," J. Lightwave Technol. 22 (1), 166-171 (2004)}

{Sandford, S. P. and Antill, C. W., "Laser frequency control using an optical resonator locked to an electronic oscillator," IEEE J. Quantum Elect. 33 (11), 1991-1996 (1997)}

A recent paper has disclosed a method of directly measuring the laser junction temperature by measuring the laser junction voltage. The junction voltage is used in a control loop to stabilize the laser temperature and emission wavelength.

{A. Asmari, J. Hodgkinson*, E. Chehura, S. E. Staines and R. P. Tatam, "Wavelength stabilisation of a DFB laser diode using measurement of junction voltage" Proc. of SPIE Vol. 9135, 91351A (2014)}

{A. Asmari, J. Hodgkinson*, E. Chehura, S. E. Staines and R. P. Tatam "A new technique to stabilise the emission wavelength of laser diodes for use in TDLS" FLAIR, 37, Florence (2014)}

This method stabilizes the laser emission wavelength but the stability is inadequate for sensitive TDL spectroscopy. The method also requires injection current modulation which could compromise the modulation levels required for sensitive WMS.

Optical interference fringes caused by reflection from optical elements degrade the sensitivity TDLS systems and causes thermal drift. A reflectivity of only 0.0025 will cause interference fringes of optical depth of 1% peak to peak.

{C. R. Webster, "Brewster-plate spoiler: a novel method for reducing the amplitude of interference fringes that limit tunable-laser absorption sensitivities" JOSA B, Vol. 2, Issue 9, pp. 1464-1470 (1985)}

In most TDLS systems reflection between the laser diode and its packaging and other optical components cause fringes within a TDLS system. Changes in the path length between optical elements and the laser, usually the result of thermomechanical changes, by as little as a fraction of a wavelength will cause the fringes and optical interference frequency to change. For example in a typical near infrared TDLS system only a one degree change in temperature changes the path between the first lens and the laser by approximately ten wavelengths. Optical interference changes caused by ambient temperature changes are consequently another important source of drift in TDLS systems. Line centering has no impact on the thermal drift caused by optical fringes in a TDLS system.

BRIEF SUMMARY

Maintaining a TDLS system in a thermally controlled ambient environment with a temperature stability of a small fraction of a degree in order to avoid system drift is very difficult and is too large, complex, and power intensive for most TDLS systems such as those used for portable applications. The applicant has invented an alternative method and apparatus to thermally stabilize a tunable diode laser spectrometer. The method may utilize two thermoelectric coolers (TEC). An inner TEC may stabilize the temperature of the laser diode element. An outer TEC stabilizes the temperature of the laser package. The inner TEC uses a Peltier element, a signal indicative of a temperature of the diode, such as from a thermistor located adjacent to the diode, and a Peltier current driver in this context functioning as a controller to form a temperature control loop so as to maintain the laser diode at a fixed temperature and consequently fix its emission wavelength. The outer TEC uses another Peltier element, thermally mounted in relation to the laser package (e.g., the laser package is thermally mounted on the Peltier element or the Peltier element is thermally mounted on the laser package), a signal indicative of a temperature of the laser package, such as from a thermistor located adjacent to the laser package, and a Peltier current driver to form a temperature control loop so as to maintain the laser package at a fixed temperature. A Peltier element not thermally mounted in relation to the laser package but otherwise arranged to influence a temperature of the laser package (e.g., a Peltier element mounted on a housing containing the laser package to influence the temperature of the interior of the housing) could also be used but would be less convenient and would likely provide a lower precision of temperature control. The method also includes means to stabilize the temperature of the TEC controlling and laser current generating circuitry as required for applications requiring precise and accurate gas concentration measurements.

The role of the inner TEC is to stabilize the temperature of the laser as practiced in the TDLS art. One role of the outer TEC is to stabilize the temperature of the laser package over a large environmental temperature range to improve the thermal stability of the inner TEC. Another role of the outer TEC is to stabilize the temperature of the laser package over a large environmental temperature range and limit laser emission frequency thermal changes and minimize system drift. Another role of the outer TEC is to stabilize the temperature of the laser package over a large environmental temperature range to limit thermal interference fringe changes and to minimize system drift.

Limiting drift by stabilizing the temperature of the electronics that control the inner and outer TECs and the laser current is necessary for high sensitivity applications. Using Peltier elements to stabilize the temperature of these electronics is considered impractical, but this should not be construed to limit the claims to exclude such an embodiment. The applicant has invented an alternative method and apparatus for stabilizing the TEC control and laser current generating circuitry. The method utilizes laser current generators and inner and outer TEC controllers all on one circuit board known as the laser driver. This laser driver circuit board has circuitry and heating resistors distributed across the surface to provide uniform resistive heating of the circuit board. The resistor currents are regulated by a computer controlled thermoelectric switch centrally located on the laser driver circuit board. Since the circuit board has no cooling means the thermoelectrically regulated temperature must be set above the maximum system temperature that occurs at the highest ambient temperature. The circuit board may be thermally insulated to minimize the influence of ambient temperature changes on heating.

It is therefore an object and an advantage of the present invention to provide an apparatus and method for thermally stabilizing a TDLS gas sensor.

It is an advantage of the present invention to provide a thermally stable TDLS gas sensor that requires no frequency reference such as a sample gas absorption cell.

It is yet another advantage of the present invention to provide a TDLS gas sensor that over a wide environmental temperature range does not have the degradation of accuracy and precision caused by line centering.

It is further advantage of the present invention to provide a TDLS gas sensor that over a wide environmental temperature range has very precise laser temperature and emission frequency stabilization.

It is a still further advantage of the present invention to provide a TDLS gas sensor that over a wide environmental temperature range has thermally stable laser current and TEC control electronics.

It is an additional advantage of the present invention to provide a portable TDLS gas sensor that is thermally stable over a wide environmental temperature.

It is to be understood that, although the applicant believes that his preferred embodiment described herein meets the objects and provide the advantages described, the scope of the invention is to be determined by reference to the claims and not necessarily by whether the embodiment achieves all objects and advantages stated.

Accordingly, there is provided a thermal control system for a packaged laser diode, the packaged laser diode having a laser package and a diode within the laser package, the thermal control system comprising an outer Peltier element located exterior to and thermally mounted in relation to the laser package, and a controller connected to the outer Peltier element and connected to receive a signal indicative of a temperature of the laser package to control the outer Peltier element according to the signal indicative of a temperature of the laser package.

In various embodiments, there may be included any one or more of the following features: There may be a heat conductive element mounted between the outer Peltier element and the laser package. There may be an outer temperature sensor mounted in the heat conductive element, the outer temperature sensor connected to the controller to provide the signal indicative of a temperature of the laser package. There may be a heat conductive cap arranged around the laser package and connected thermally to the heat conductive element. There may be thermal insulation arranged around the heat conductive cap. There may be thermal insulation arranged around the laser package. There may be a further controller connected to an inner Peltier element located within the laser package, the further controller connected to receive a signal indicative of a temperature of the diode to control the inner Peltier element according to the signal indicative of a temperature of the diode. The signal indicative of a temperature of the diode may be provided by an inner temperature sensor located in proximity to the diode.

In a further embodiment there is provided a thermal control system for a packaged laser diode, the packaged laser diode having a laser package and a diode within the laser package, the thermal control system comprising an outer Peltier element located exterior to the laser package, and arranged to influence a temperature of the laser package, a controller connected to the outer Peltier element and connected to receive a signal indicative of the temperature of the laser package to control the outer Peltier element according to the signal indicative of the temperature of the laser package, and a further controller connected to an inner Peltier element located within the laser package, the further controller connected to receive a signal indicative of a temperature of the diode to control the inner Peltier element according to the signal indicative of a temperature of the diode.

In various embodiments, there may be included any one or more of the following features: the signal indicative of a temperature of the diode may be provided by an inner temperature sensor located in proximity to the diode. There may be a heat conductive cap arranged around the laser package. There may be thermal insulation arranged around the heat conductive cap. There may be thermal insulation arranged around the laser package.

All of the above described embodiments, unless otherwise stated, may include any one or more of the following features: there may be a temperature controlled circuit board and a laser driver mounted on the temperature controlled circuit board, the laser driver connected to drive the diode. In embodiments where there is a further controller, the further controller may be mounted on the temperature controlled circuit board. The controller may be located on the temperature controlled circuit board. The temperature controlled circuit board may be temperature controlled using heating resistors controlled according to a temperature sensor mounted on the temperature controlled circuit board. The circuit board may be thermally insulated.

These and other aspects of the device and method are set out in the claims, which are incorporated here by reference.

BRIEF DESCRIPTION OF THE DRAWINGS

Embodiments will now be described with reference to the figures, in which like reference characters denote like elements, by way of example, and in which.

DETAILED DESCRIPTION

Figure 1:
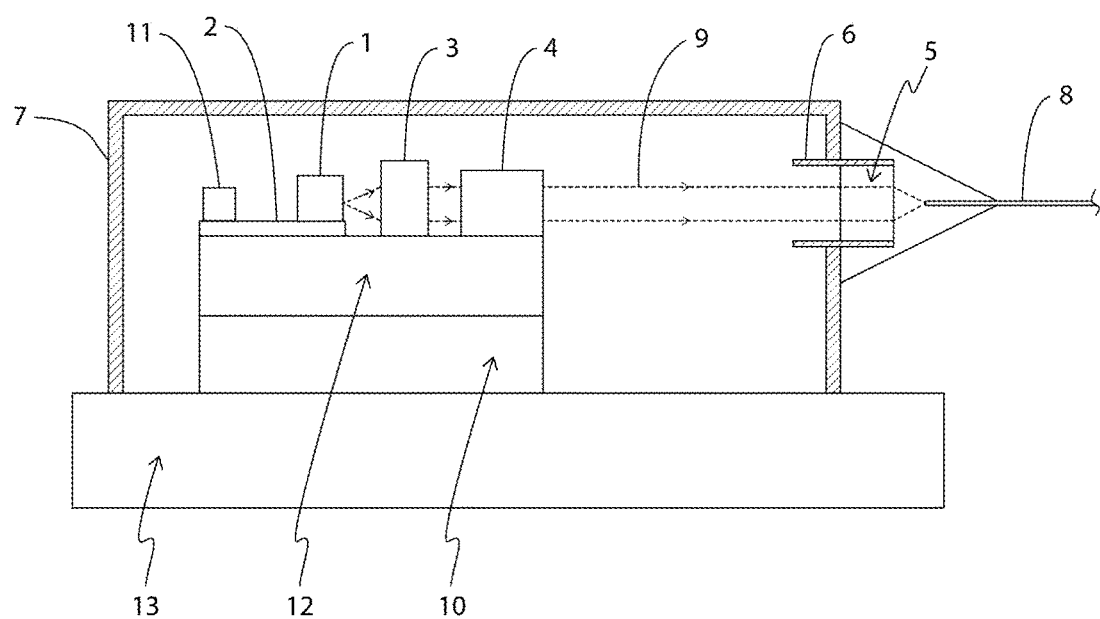
FIG. 1 is a functional schematic of a Butterfly packaged laser.

FIG. 1 is a functional schematic of a prior art Butterfly packaged laser diode typical of those used for TDLS gas sensing. Referring to this drawing, the laser 1 is mounted on a ceramic submount 2. Collimating lens 3, which is mounted on the copper thermal header 12, collects and collimates the laser beam from the laser. Opto-isolator 4 is also mounted on the copper header. Focusing lens 5 is mounted in a cylindrical tube 6 attached to the wall of the Butterfly package 7. The fibreoptic pigtail 8 is attached to the wall of the Butterfly package. The collimated laser beam 9 passes through the opto-isolator and is focused onto the fibreoptic pigtail. The copper thermal header is attached to a Peltier element 10 which is thermally attached to the Butterfly case. Thermistor 11 is attached to the ceramic submount in close proximity to the laser. The Butterfly package is thermally mounted on a heat sink 13.

Figure 2:
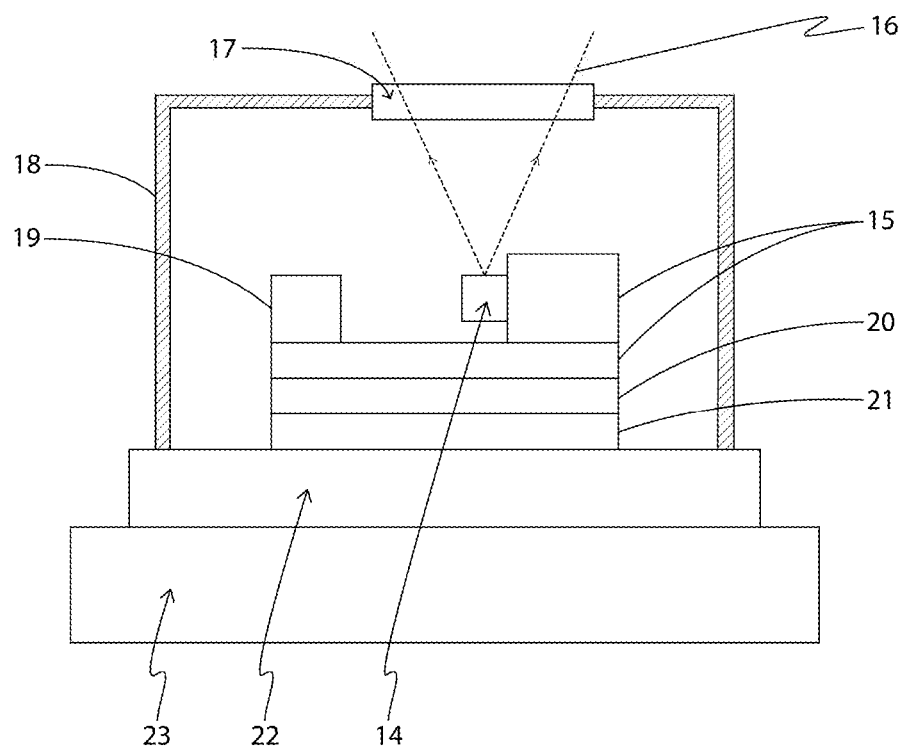
FIG. 2 is a functional schematic of a TO packaged laser.

FIG. 2 is a functional schematic of a prior art TO packages laser typical of those used in TDLS gas sensors. Referring to this drawing, laser 14 is attached to ceramic submount 15. The uncollimated laser beam 16 passes through window 17 mounted in the case of the TO package 18. Thermistor 19 is mounted on the ceramic submount in close proximity to the laser. The ceramic submount is attached to the copper thermal header 20 which is thermally mounted on the Peltier element 21. The Peltier element is attached to the base 22 of the TO package and the TO package is mounted on the heat sink 23.

Figure 3:
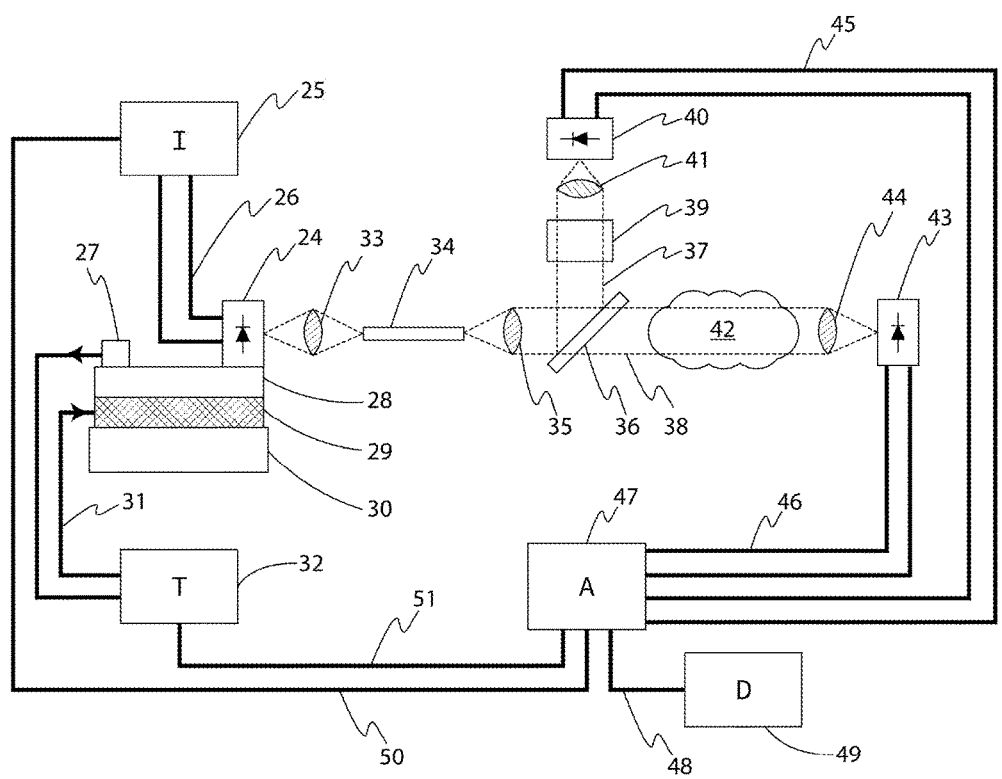
FIG. 3 is a functional schematic of a TDLS gas detector with a Butterfly packaged laser.

FIG. 3 is a functional schematic of a prior art TDLS gas detector with a Butterfly packaged laser. Laser diode 24 is connected electrically 26 to a current source 25 that generates the offset bias and modulation injection currents. The laser and thermistor 27 are mounted on a ceramic submount and copper thermal header 28 and this header is thermally mounted on a Peltier element 29 and the Peltier element is mounted thermally on a heat sink 30 as shown in more detail in FIG. 1. The Peltier element and the thermistor are connected electrically 31 to a TEC driving circuit 32. The laser beam is focused by optics 33 onto a fibreoptic pigtail 34. The laser beam emerging from the fibreoptic is collimated by the collimating lens 35 and the collimated beam is split by beam splitter 36 into a reference beam 37 and a target gas beam 38. The reference beam passes through a gas reference cell 39 and is then focused onto the reference photodiode 40 by lens 41. The target gas bam passes through sample gas 42 and is then focused onto the target gas photodiode 43 by the lens 44. Current from the reference photodiode 45 and the current 46 from the sample photodiode flow to the analyzer 47 that calculates the concentration of the target gas. Gas concentration data from the analyzer are communicated through a user interface 48 to data storage and display circuitry 49. The analyzer controls the current source 50 and TEC driver 51.

Figure 4:
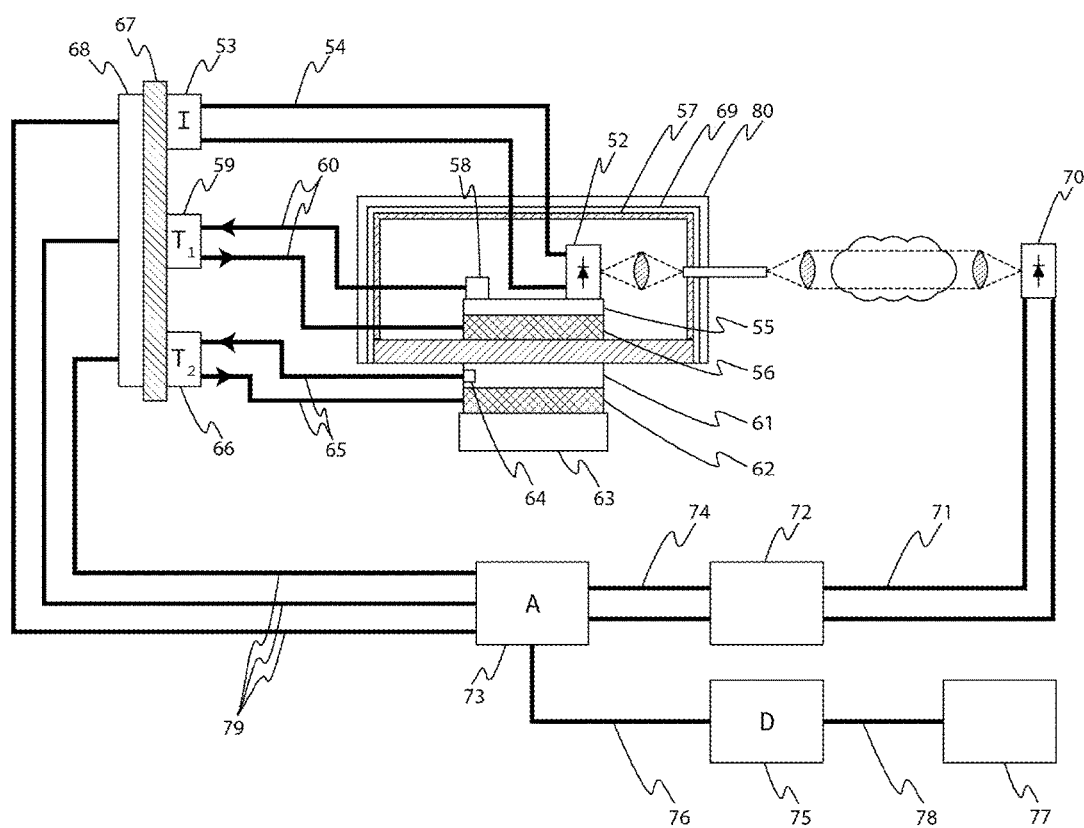
FIG. 4 is a functional schematic of the invented TDLS gas detector with a Butterfly packaged laser.

FIG. 4 is a functional schematic of the preferred embodiment of the invented TDLS gas detector with a Butterfly packaged laser. This invention may also be applied to any other packaged laser including for example a TO packaged laser. Laser 52 is connected to the current supply 53 by conductors 54. The laser is mounted on the ceramic submount 55 which is in turn mounted on an inner Peltier cooler 56. The inner Peltier cooler is mounted on the base of a Butterfly package 57. The thermistor element 58 and the inner Peltier cooler are connected to a TEC driving circuit 59 through conductors 60 to form a feedback temperature control loop. This feedback loop regulates the temperature of the thermistor and laser with an accuracy of +/−1 mK. The Butterfly package is mounted on a copper heat spreader 61 which conducts heat from the package. The butterfly package is thermally insulated by insulation 80 on all surfaces other than the surface of the base covered by the heat spreader. This insulation 80 maintains the Butterfly package at an essentially uniform temperature. The heat spreader is mounted on an outer Peltier cooler 62 which in turn is mounted on the heat sink 63. A second thermistor 64 is mounted in the copper heat spreader. The second thermistor and outer Peltier cooler are connected by conductors 65 to a second TEC driving circuit 66 to form a feedback temperature control loop. This feedback loop regulates the temperature of the thermistor and hence the heat spreader with an accuracy of +/−5 mK for an ambient temperature change from −40 C to 50 C. Stabilization of the temperature of the Butterfly package by the heat spreader ensures that the laser temperature and hence emission frequency remain constant over an ambient temperature change of −40 C to 50 C. It would also be possible to use a temperature sensor located other than in the heat spreader, for example a temperature sensor inside the laser package separate from the temperature sensor used by the inner TEC. An alternative solution which does not require an additional temperature sensor would be to use the output of the inner TEC driving circuit 59 as the signal used to control the feedback loop for the outer TEC driving circuit 66. This output is also a signal indicative of a temperature of the laser package as the amount of heating or cooling required by the inner TEC to keep the thermistor 58 at constant temperature depends on the temperature of the laser package. In another embodiment, it may be desired to omit the inner TEC, accepting a lower degree of control of the laser diode temperature. In such an embodiment, the outer TEC could use a signal from thermistor 58 as the signal used to control the feedback loop for outer TEC driving circuit 66. In such an embodiment in which the inner TEC is not present or not operational, the signal from thermistor 58 is a signal indicative of the temperature of the laser package as well as of the laser diode. When the inner TEC is operational and controlled according to the signal from thermistor 58, the outer TEC should not be controlled according to the signal from thermistor 58 since two control circuits controlling the same signal can result in instabilities.

The laser current source 53, first TEC control circuit 59, and second TEC control circuit 66 are mounted in close proximity on a laser driver circuit board 67. This circuit board has an array of heating resistors 68 dispersed across the populated surface. This array is combined with a circuit board mounted thermistor and relay to form a temperature control feedback loop which stabilizes the temperature of the laser driver board over a range of ambient temperatures. The circuit board may also be thermally insulated. When the temperature of the laser driver board is set above the highest ambient temperature, this feedback control loop stabilizes the temperature of the laser driver board to an accuracy of +/−50 mK.

The walls and top of a butterfly package are typically fabricated from poor conductivity thin steel sheet. In the preferred embodiment thermal stabilization of the butterfly package is enhanced with a heat conductive cap arranged around the laser package such as thin walled copper cap 69. This cap is connected thermally to the copper spreader and maintains the body of the butterfly package at the temperature of the heat spreader with less insulation than is required without a copper cap. In an embodiment where the heat conductive cap is present, the thermal insulation 80 may be arranged around the heat conductive cap.

In operation of the TDLS system, light from the laser is transmitted through a fibreoptic, through a gas to be measured, and is collect by a photodiode 70 as in prior art TDL gas sensors. The optical path may also be made up of a transceiver as commonly practiced in the TDL gas sensing art. The photodiode current passes through a coaxial cable 71 to a transimpedance circuit 72 which converts the photodiode current to a voltage of several volts. This photodiode voltage is communicated to an analyzer circuit 73 through a conductor 74. The preferred conductor is a shielded CAT6 cable typically used for telephone communication and may be several hundreds of meters in length, if required. The analyzer circuit uses the photodiode voltage to calculate the gas concentration on the gas measurement path as practiced in the TDL gas sensing art. Various analyzer circuits may be used but the preferred analyzer circuit is a digital circuit. The analyzer sets the temperature operating point of the two TEC controlling circuits and sets the laser currents from the laser current generating circuit through conductors 79. Many different types of conductor may be used but the preferred conductor is a ribbon cable. The operating parameters of the analyzer are controlled by user interface circuit 75 through conductors 76. The analyzer measurements are also communicated to the user interface circuit by the conductor 75.

Many different user interface circuits may be used to both display measurement results and control the TDLS gas sensor but the preferred circuit is a flat panel display. Measurement results may be communicated to external data collecting systems 77 through cable or wireless circuitry 78.

Immaterial modifications may be made to the embodiments described here without departing from what is covered by the claims.

In the claims, the word "comprising" is used in its inclusive sense and does not exclude other elements being present. The indefinite articles "a" and "an" before a claim feature do not exclude more than one of the feature being present. Each one of the individual features described here may be used in one or more embodiments and is not, by virtue only of being described here, to be construed as essential to all embodiments as defined by the claims.

The embodiments of the invention in which an exclusive property or privilege is claimed are defined as follows:

1. A thermal control system for a packaged laser diode, the packaged laser diode having a laser package and a diode within the laser package, the thermal control system comprising:
    an outer Peltier element located exterior to and thermally mounted in relation to the laser package;
    a controller connected to the outer Peltier element and connected to receive a signal indicative of a temperature of the laser package to control the outer Peltier element according to the signal indicative of a temperature of the laser package; and
    a further controller connected to an inner Peltier element located within the laser package, the further controller connected to receive a signal indicative of a temperature of the diode to control the inner Peltier element according to the signal indicative of a temperature of the diode.

2. The thermal control system of claim 1 further comprising a heat conductive element mounted between the outer Peltier element and the laser package.

3. The thermal control system of claim 2 further comprising an outer temperature sensor mounted in the heat conductive element, the outer temperature sensor connected to the controller to provide the signal indicative of a temperature of the laser package.

4. The thermal control system of claim 1 further comprising thermal insulation arranged around the laser package.

5. The thermal control system of claim 1 in which the signal indicative of a temperature of the diode is provided by an inner temperature sensor located in proximity to the diode.

6. A kit comprising at least a controller for a Peltier element and instructions to assemble a thermal control system as defined in claim 1 or a reference indicating how to find instructions to assemble a thermal control system as defined in claim 1.

7. The thermal control system of claim 1 in which the controller and further controller together comprise a laser driver.

8. The thermal control system of claim 7 in which the laser driver is mounted on one circuit board.

9. A thermal control system for a packaged laser diode, the packaged laser diode having a laser package and a diode within the laser package, the thermal control system comprising:
    an outer Peltier element located exterior to and thermally mounted in relation to the laser package;
    a controller connected to the outer Peltier element and connected to receive a signal indicative of a temperature of the laser package to control the outer Peltier element according to the signal indicative of a temperature of the laser package;
    a heat conductive element mounted between the outer Peltier element and the laser package; and
    a heat conductive cap arranged around the laser package and connected thermally to the heat conductive element.

10. The thermal control system of claim 9 further comprising thermal insulation arranged around the heat conductive cap.

11. A thermal control system for a packaged laser diode, the packaged laser diode having a laser package and a diode within the laser package, the thermal control system comprising:
    an outer Peltier element located exterior to the laser package, and arranged to influence a temperature of the laser package;
    a controller connected to the outer Peltier element and connected to receive a signal indicative of the temperature of the laser package to control the outer Peltier element according to the signal indicative of the temperature of the laser package; and
    a further controller connected to an inner Peltier element located within the laser package, the further controller connected to receive a signal indicative of a temperature of the diode to control the inner Peltier element according to the signal indicative of a temperature of the diode.

12. The thermal control system of claim 11 in which the signal indicative of a temperature of the diode is provided by an inner temperature sensor located in proximity to the diode.

13. The thermal control system of claim 11 further comprising a heat conductive cap arranged around the laser package.

14. The thermal control system of claim 13 further comprising thermal insulation arranged around the heat conductive cap.

15. The thermal control system of claim 11 further comprising thermal insulation arranged around the laser package.

16. The thermal control system of claim 11 in which the controller and further controller together comprise a laser driver.

17. The thermal control system of claim 16 in which the laser driver is mounted on one circuit board.

18. A thermal control system for a packaged laser diode, the packaged laser diode having a laser package and a diode within the laser package, the thermal control system comprising:
    an outer Peltier element located exterior to and thermally mounted in relation to the laser package;
    a controller connected to the outer Peltier element and connected to receive a signal indicative of a temperature of the laser package to control the outer Peltier element according to the signal indicative of a temperature of the laser package;
    a further controller connected to an inner Peltier element located within the laser package, the further controller connected to receive a signal indicative of a temperature of the diode to control the inner Peltier element according to the signal indicative of a temperature of the diode; and a temperature controlled circuit board and a laser driver mounted on the temperature controlled circuit board, the laser driver connected to drive the diode, and the laser driver including the controller and further controller.

19. The thermal control system of claim 18 in which the further controller is mounted on the temperature controlled circuit board.

20. The thermal control system of claim 18 in which the controller is located on the temperature controlled circuit board.

21. The thermal control system of claim 18 in which the temperature controlled circuit board is temperature controlled using heating resistors controlled according to a temperature sensor mounted on the temperature controlled circuit board.

22. The thermal control system of claim 18 in which the circuit board is thermally insulated.

* * * * *